(12) United States Patent
Becker et al.

(10) Patent No.: US 9,271,872 B2
(45) Date of Patent: Mar. 1, 2016

(54) WELDING HELMET AIR FLOW BARRIER

(75) Inventors: William Joshua Becker, Manitowoc, WI (US); Eric Sommers, Appleton, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 1549 days.

(21) Appl. No.: 12/390,980

(22) Filed: Feb. 23, 2009

(65) Prior Publication Data

US 2009/0210988 A1 Aug. 27, 2009

Related U.S. Application Data

(60) Provisional application No. 61/031,415, filed on Feb. 26, 2008.

(51) Int. Cl.
*A61F 9/06* (2006.01)

(52) U.S. Cl.
CPC ........................................ *A61F 9/068* (2013.01)

(58) Field of Classification Search
CPC ......................................................... A61F 9/06
USPC .............................................................. 2/8.6
See application file for complete search history.

(56) References Cited

U.S. PATENT DOCUMENTS

| 2,029,566 | A | * | 2/1936 | Herzer | 128/201.25 |
|---|---|---|---|---|---|
| 3,649,964 | A | * | 3/1972 | Schoelz et al. | 128/205.25 |
| 3,822,698 | A | * | 7/1974 | Guy | 128/201.25 |
| 4,573,217 | A | * | 3/1986 | Reed | 2/7 |
| 4,730,612 | A | * | 3/1988 | Dampney | 128/201.24 |
| 4,752,974 | A | * | 6/1988 | Haino | 2/424 |
| 5,009,225 | A | * | 4/1991 | Vrabel | 128/201.24 |
| 5,054,480 | A | * | 10/1991 | Bare et al. | 128/201.25 |
| 5,592,936 | A | * | 1/1997 | Thomas et al. | 128/206.12 |
| 5,628,308 | A | * | 5/1997 | Harges et al. | 128/206.21 |
| 5,890,236 | A | * | 4/1999 | Harges et al. | 2/440 |
| 6,006,360 | A | * | 12/1999 | Reed | 2/202 |
| 6,328,031 | B1 | * | 12/2001 | Tischer et al. | 128/201.25 |
| 6,338,340 | B1 | * | 1/2002 | Finch et al. | 128/205.27 |
| 6,370,695 | B2 | * | 4/2002 | Paris et al. | 2/171.3 |
| 6,990,691 | B2 | * | 1/2006 | Klotz et al. | 2/171.3 |
| 7,534,005 | B1 | * | 5/2009 | Buckman | 362/105 |
| 2004/0004196 | A1 | * | 1/2004 | DeMeo et al. | 250/516.1 |
| 2006/0107431 | A1 | * | 5/2006 | Curran et al. | 2/7 |
| 2008/0184996 | A1 | * | 8/2008 | Colorado | 128/201.25 |
| 2010/0043725 | A1 | * | 2/2010 | Hall | 119/850 |
| 2010/0125934 | A1 | * | 5/2010 | Green | 2/424 |

* cited by examiner

*Primary Examiner* — Brian D Nash
(74) *Attorney, Agent, or Firm* — Fletcher Yoder P.C.

(57) ABSTRACT

An air barrier that prevents entrainment of surrounding air from the welding environment into the welding helmet is provided. The barrier for the welding helmet contains a flexible curtain, front and rear edges, and means for securing the front edge of the curtain adjacent to the rear edge of the helmet. The flexible curtain may be made of fire-resistant and flexible molded material. The air barrier may be permanently secured to or removable from the welding helmet. The invention may be used in conjunction with a variety of ventilation and cooling systems, including small units that mount on or in welding helmets, as well as more elaborate blowing systems partially carried by the welder.

20 Claims, 4 Drawing Sheets

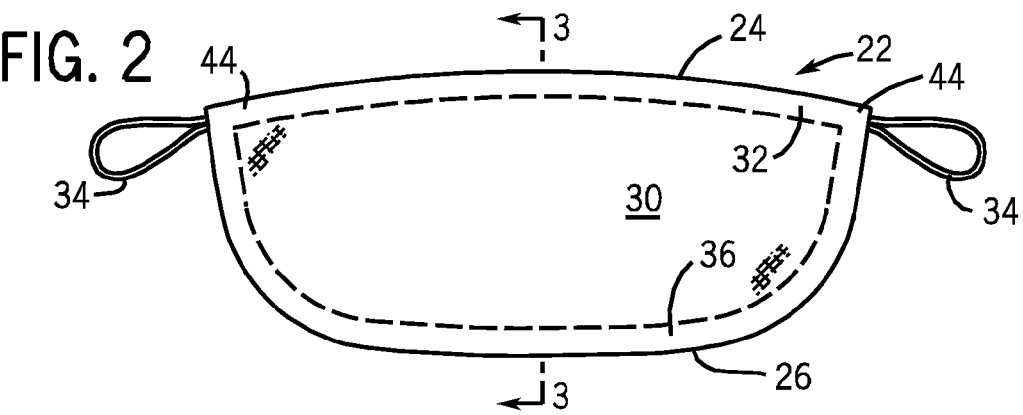
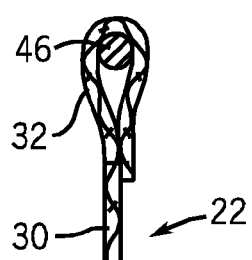
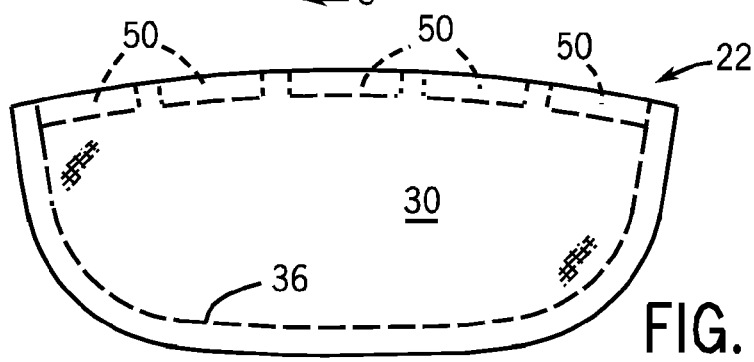
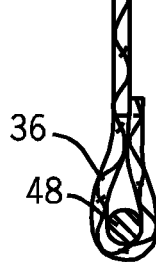
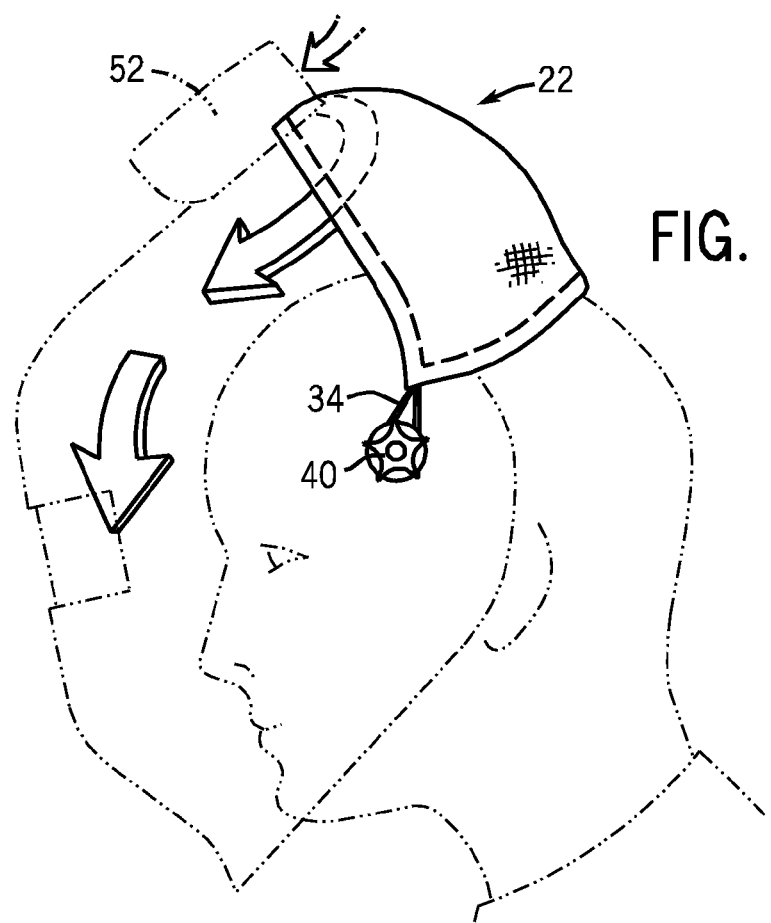

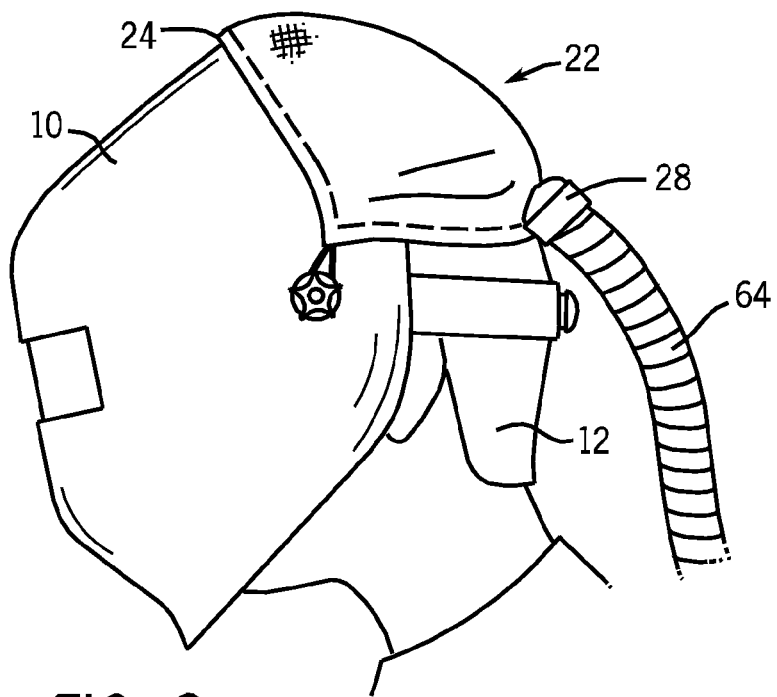
FIG. 9
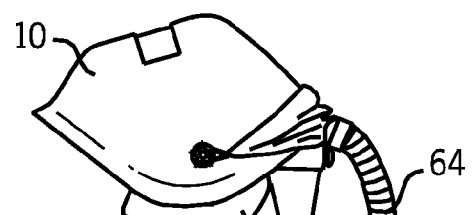
FIG. 8
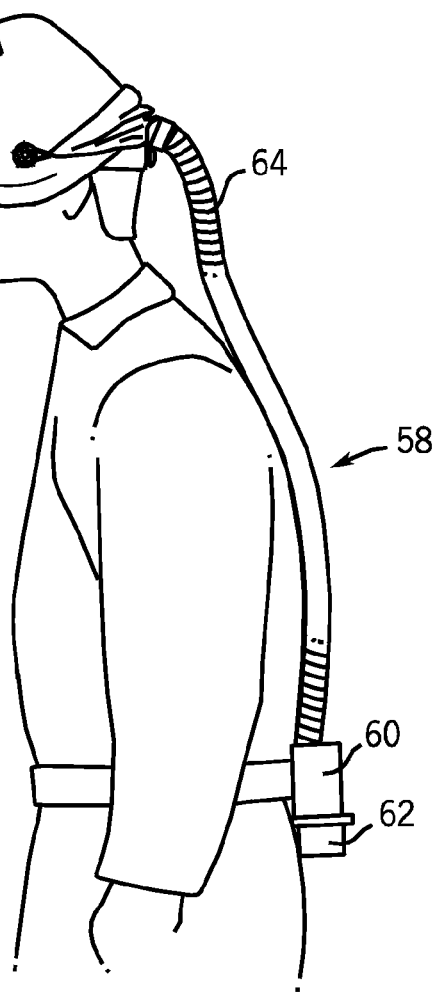

WELDING HELMET AIR FLOW BARRIER

CROSS REFERENCE TO RELATED APPLICATIONS

This application is a Non-provisional patent application of U.S. Provisional Patent Application No. 61/031,415, entitled "Helmet Cooling and Air-Filtering System", filed Feb. 26, 2008, which is herein incorporated by reference.

BACKGROUND

The invention relates generally to welding helmets, and more particularly to arrangements for controlling the influx of air into a welding helmet.

Welding can be a heat intensive process, especially during the summer months in outdoor locations or in plants without air conditioning or good air circulation. Furthermore, welding environments contribute fumes and particulates to the locations in which welding is performed. While some industrial standards exist that require powered air purifying respirator (PAPR) systems, such standards may not apply to all situations in which improved air circulation may be desirable for operator comfort, particularly over extended periods of work. Moreover, when not required, PAPR systems represent a relatively costly approach to ventilation and cooling.

Certain relatively lower cost, lightweight airflow systems have been proposed that can be mounted to the welding helmet, and that offer a promising solution to this problem. However, these systems are often less than satisfactory, in particular due to the potential for entrainment of surrounding air from the welding environment into the welding helmet. Therefore, there exists a need for improvements in such systems that prohibit outside air from degrading the air quality in the helmet.

BRIEF DESCRIPTION

The present invention provides methods and devices designed to respond to such needs. The invention may be used in conjunction with a variety of ventilation and cooling systems, including small units that mount on or in welding helmets, as well as more elaborate blowing systems partially carried by the welder. The invention provides an air barrier for a welding helmet that prevents or reduces the intrusion of surrounding air into the helmet from the welding environment. The barrier for the welding helmet contains a flexible curtain, front and rear edges, and means for securing the front edge of the curtain adjacent to the rear edge of the helmet. These means may include, inter alia, elastic bands, hook and loop fastener arrangements, and so forth. Certain embodiments may include minor alterations, such as apertures, designed to outfit the barrier for use with multiple airflow systems of various design.

DRAWINGS

These and other features, aspects, and advantages of the present invention will become better understood when the following detailed description is read with reference to the accompanying drawings in which like characters represent like parts throughout the drawings, wherein:

FIG. 2 is a front view of the barrier of FIG. 1, removed from the welding helmet of FIG. 1;

FIG. 3 is a cross sectional view of the barrier of FIG. 2 illustrating elastic cords in hems on either edge to facilitate placement of the barrier in use;

FIG. 4 is a front view of the barrier of FIG. 1 illustrating the use of a hook and loop fastener system for attachment to the welding helmet;

FIG. 5 is a side view of a welder wearing a welding helmet with an air barrier of FIG. 1 and a clip-on exterior ventilation unit;

FIG. 8 is a side view of a welder wearing a welding helmet attached to an external ventilation system;

FIG. 9 is a side view of a welder wearing a welding helmet with an air barrier and the ventilation system of FIG. 8.

DETAILED DESCRIPTION

Figure 1:
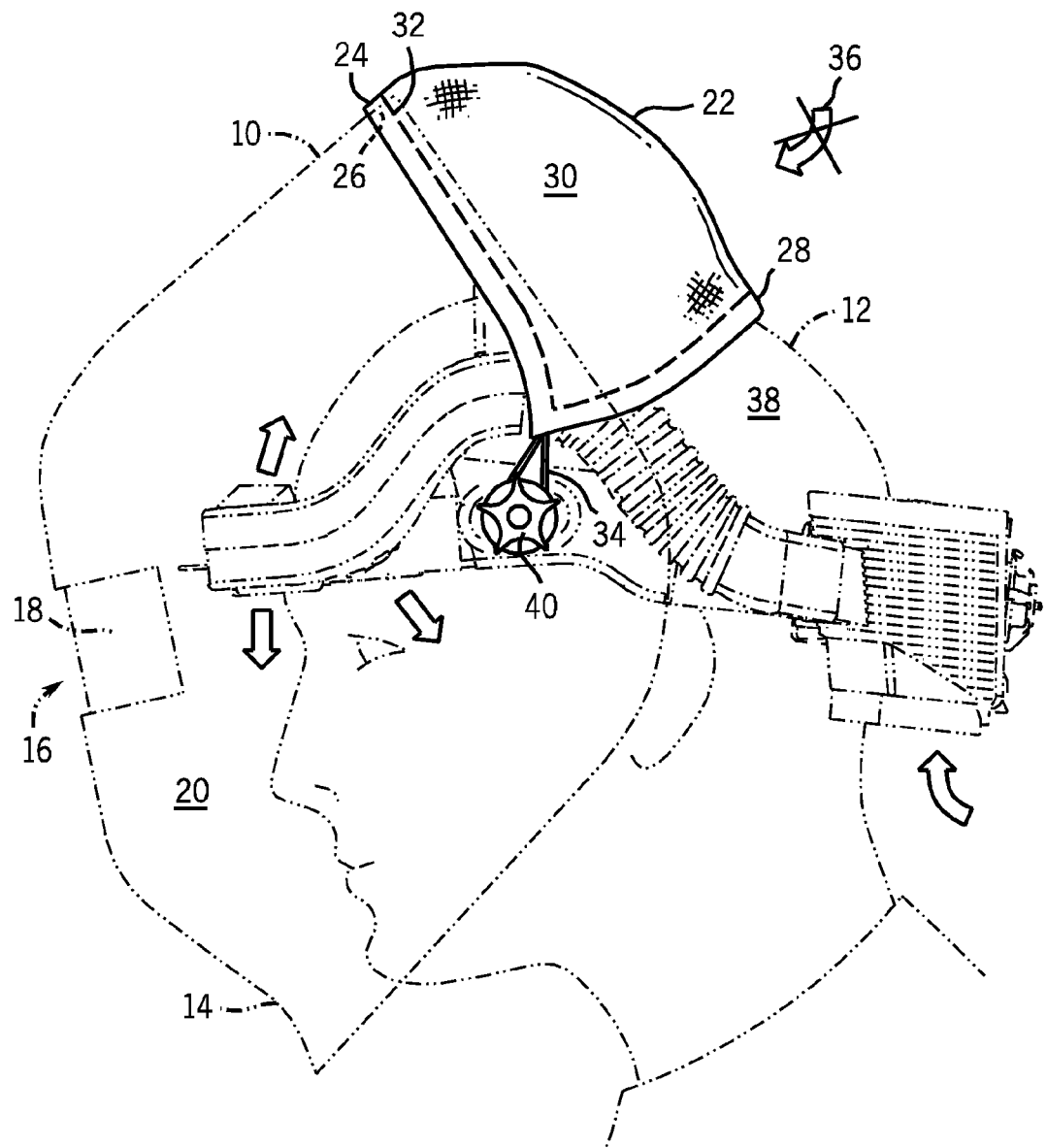
FIG. 1 is a side view of a welder wearing a welding helmet with an air barrier and an airflow system in accordance with aspects of the present invention.

FIG. 1 illustrates a welding helmet 10 that is worn on the head 12 of a welder. The welding helmet 10 may be attached to a shield 14, which covers the face of the welder during welding. The shield 14 contains a visor 16 with an embedded dark or autodarkening lens 18 through which the welder can view the welding process. The area between the shield 14 and the head of the welder 12 is a volume 20 where air can flow. In the various embodiments of the invention described below, a forced air system is provided that blows fresh filtered air across the face of the welder within the inner volume 20. An air barrier 22 in the form of a flexible curtain prevents the entrainment of surrounding air from the welding environment. As described below, the barrier 22 may be removable from the helmet 10, and may be designed as an add-on item that a welder can affix to the helmet for use with a ventilation system to prevent unfiltered outside air from being drawn into the inner volume of the helmet.

The front edge 24 of the barrier 22 can be formed either on or in the curtain 30 and urges the flexible curtain towards the welding helmet 10. In certain embodiments, the front edge 24 may be elastic. As illustrated, when the curtain is in place on the helmet, the rear edge 26 of the helmet is disposed immediately adjacent to the front edge 24 of the curtain 30. The rear edge 28 of the curtain 30 extends out above the head of the welder 12. This curtain 30 may be constructed of fire resistant, flexible material, such as a 200 denier nylon with 1.5 ounce per square yard urethane coating that meets an industry standard fire test for flame propagation specification NFPA 701-89, although other materials may be used. The elastic front edge 24 includes a hem 32 with an elastic band disposed in it. In the illustrated embodiment, the elastic band terminates on either side with loops or hooks that can be wrapped around helmet head gear features, such as adjustment knobs 40 on either side of the helmet. Furthermore, this elastic edge 24 urges the flexible curtain 30 towards the helmet, preferably just forward of the rear edge thereof. Loops 36 serve to secure the entire structure to the helmet, yet allow it to be very easily removed when desired. This hook and loop system allows for the barrier 22, secured to the head of the welder 12, to prevent air flow 42 from the welding environment from entering the volume 20 inside the helmet 10 of the welder.

FIG. 2 illustrates the curtain 30 detached from the headgear with the aforementioned loops 34. As mentioned above, the loops 34 (or other attachment structures), allow the curtain to be removably secured to an adjustment knob on either side of the head of the welder 12. Other attachment mechanisms may be envisaged, and where desired the curtain may form a permanent part of the helmet or headgear assembly. In the illustrated embodiment, the first hem 32 and the second hem 36 meet at the corners 44 of the curtain 30, where the elastic loops 34 extend outward on either side. FIG. 3 is a cross sectional view along line 3-3 of FIG. 2. As can be seen in this view, the barrier 22 is comprised of the curtain 30 extending between the first hem 32 and the second hem 36. The hems may be formed by rolling the fabric of the curtain and stitching to form an elongated opening. Each hem contains a respective elastic cord, as illustrated, including a first elastic cord 46 and a second elastic cord 48, which extend out to form the loops that secure the curtain 30 to the helmet.

Other attachment arrangements for securing the curtain 30 to or near the rear edge of the helmet may include hook and loop fasteners, glue, rivets, snaps, buttons, and so forth. For example, as shown in FIG. 4, hook/loop fastener arrangements may include strips or tabs 50 made of either a hook or a loop component of such a system, with the complementary component (loop or hook) being secured to the helmet (not shown). As will be recognized by those skilled in the art, some welding helmets will not be conducive to retaining an air barrier by elastic biasing towards the helmet alone. As a further alternative to the securement arrangements discussed above, one or more clips may be used that would firmly grasp or capture a portion of the helmet, such as adjacent to the rear edge.

It should also be noted that the air barrier may terminate at various locations between the rear edge of the helmet and the head gear used to retain the helmet on the head of the welder. That is, as will be appreciated by those skilled in the art, such welding helmets generally include a band that surrounds the welder's head, the size of which may typically be adjusted by slides or a knob located along the rear of the band (see, e.g., FIG. 1). The rear of the air barrier may terminate in the vicinity of this head gear band, and may be secured to the band, where desired. Alternatively, as described above, the barrier may terminate at a location between the head gear and the rear edge of the helmet. In both cases, the barrier is considerably shorter and cooler than covers used with existing systems, such as conventional PAPR ventilating systems.

Figure 6:
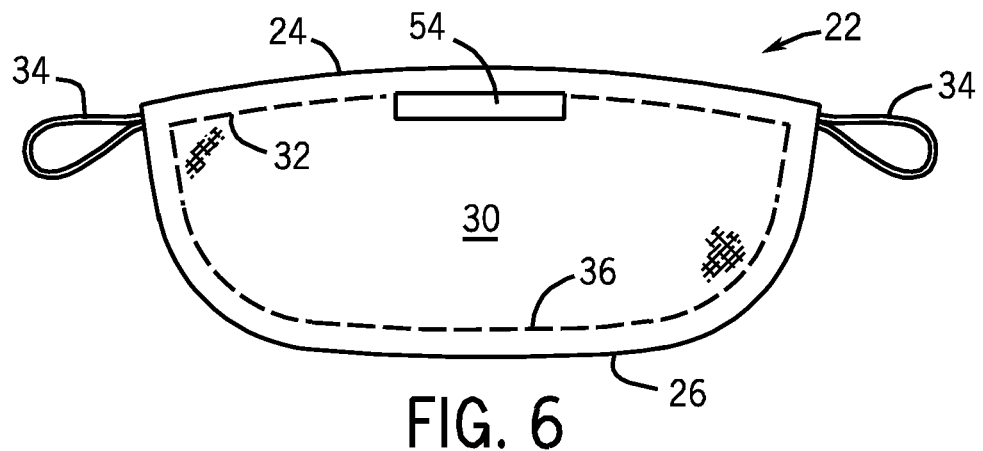
FIG. 6 is a front view of the barrier of FIG. 5 illustrating an aperture in the barrier to accommodate an air flow conduit of the clip-on unit.
Figure 7:
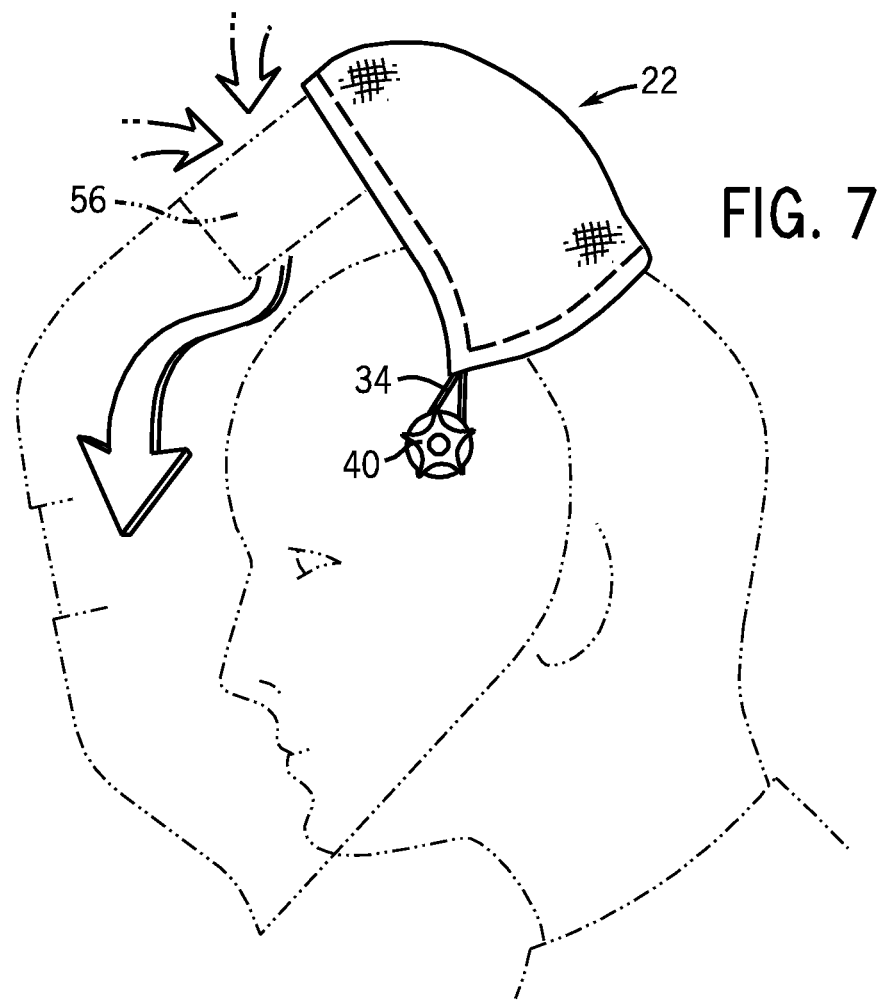
FIG. 7 is a side view of a welder wearing a welding helmet with an air barrier of FIG. 1 and an internal ventilation unit.

The air barrier 22 may be adapted for use with multiple types of airflow systems that circulate air into and through the inner volume 20 between the head of the welder 12 and the welding helmet 10. FIG. 5 illustrates an airflow system in which a clip-on unit 52 is added as an auxiliary system to the welding helmet 10, and that draws in outside air and blows the air through the volume 20 to cool the welder. Because such systems will typically include one or more conduits that extend from the unit into the inner volume 20, accommodation may be made in the air barrier for such conduits. In this embodiment, the barrier 22, illustrated in FIG. 6, includes an aperture 54 to facilitate passage of such a conduit. The conduit may simply be positioned through the aperture when the clip-on unit and barrier are mounted to the helmet. The flexible material around the aperture provide a sufficient seal to reduce or eliminate the inflow of air into the helmet through the opening The air barrier 22 can also be used with a similar system as shown in FIG. 7. In this embodiment, the helmet has been fitted with an interior blower unit 56 that draws in outside air, such as through one or more holes or openings formed in the shell of the helmet. The air may be directed to flow through the volume 20 to cool the welder, while the barrier, as before, prevents drawing unfiltered air through the opening between the helmet and the head of the welder.

The air barrier 22 can also be used to exclude outside air from contaminating the ventilation system 58 shown in FIG. 8. The system shown in FIG. 8 includes a battery/blower unit 60 that draws outside air through a filter 62 from the back of the welder, which is typically cleaner than environmental air closer to the welding location. The battery/blower unit 62 may, as in the illustrated embodiment, be worn by the welder, such as on the welder's belt, or a dedicated belt. The unit is connected to a conduit 64, which feeds filtered air into the welding helmet 10. FIG. 9 is a somewhat more detailed view of such a system when outfitted with the air barrier 22. As in the previous embodiments, the front edge 24 of the barrier 22 fits snuggly to the rear edge of the welding helmet 10, while the rear edge 28 is biased towards the back of the head of the welder 12.

It should be noted that, depending upon the material used to form the air barrier, the barrier may collapse or bunch when the helmet is moved to a raised position, as generally shown in FIG. 8. This may generally be the case for various fabrics, and the foregoing arrangements illustrated in the other figures may perform similarly. It is believed that such barriers will prove to be lighter, cooler and more comfortable to wear. Alternatively, however, the air barrier may be made of a semi-rigid material that generally retains its shape and form when the helmet is moved. Still further, certain designs presently contemplated may include a number of louvers, interleaving elements, telescoping elements, or accordion-like elements that collapse when the helmet is raised, and that expand or move with respect to one another when the helmet is lowered to a working position.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system comprising:
a welding helmet comprising a rear edge adjacent an open back portion; and
an air barrier that in operation is secured to the welding helmet, wherein the air barrier comprises:
a curtain that in operation is secured to the rear edge of the welding helmet to hold the curtain on the welding helmet and extends only over an upper part of the head of a welder rear of the helmet when the helmet is in an operative position for welding; and
an edge formed on or in the curtain that in operation extends to rear head gear that serves to hold the helmet on the head of the welder or to a location on the head of the welder between the head gear and the rear edge of the welding helmet.

2. The system of claim 1, wherein the curtain is made of a fire-resistant fabric.

3. The system of claim 1, wherein the curtain is made of a flexible molded material.

4. The system of claim 1, comprising an elastic front edge formed on or in the curtain and configured to urge the curtain towards the welding helmet.

5. The system of claim 4, comprising a pair of securement members extending from the edge and configured to hook to a structure of the helmet to hold the front edge of the curtain adjacent to the rear edge of the helmet.

6. The system of claim 1, comprising a hook and loop fastener arrangement on a front edge of the curtain and the rear edge of the helmet configured to hold the front edge of the curtain adjacent to the rear edge of the helmet.

7. The system of claim 1, wherein the edge includes a hem formed in the curtain and an elastic band disposed in the hem.

8. The system of claim 1, wherein the barrier is removably secured to the helmet.

9. A system comprising:
a welding helmet comprising a rear edge adjacent an open back portion; and
an air barrier that in operation is secured to the welding helmet, wherein the air barrier comprises:
a flexible curtain made of a fire-resistant fabric and that in operation is secured only to the rear edge of the welding helmet to hold the curtain on the welding helmet and extends only to a location on an upper part of the head of a welder when the helmet is in an operative position for welding;
a front edge formed on or in the curtain that in operation urges the curtain towards the rear edge of the helmet; and
an elastic rear edge formed on or in the curtain that in operation urges the flexible curtain towards the upper part of the head of the welder.

10. The system of claim 9, comprising a pair of securement members extending from the front edge and configured to hook to a structure of the helmet to hold the front edge of the curtain adjacent to the rear edge of the helmet.

11. The system of claim 10, wherein the securement members include elastic loops configured to be disposed around adjustment knobs on sides of the helmet.

12. The system of claim 9, wherein the elastic rear edge includes a hem formed in the curtain and an elastic band disposed in the hem.

13. The system claim 9, wherein the barrier is removably secured to the helmet.

14. A system, comprising:
a welding helmet comprising a rear edge and an open back portion and that in operation is positioned in an operative position for welding; and
an air barrier that in operation is removably attached to the welding helmet, wherein the air barrier comprises:
a curtain that in operation is secured to the rear edge of the welding helmet to hold the curtain on the welding helmet and to extend only over an upper part of the head of a welder rear of the helmet to enclose the open back portion of the welding helmet when the welding helmet is in the operative position for welding; and
an edge formed on or in the curtain that in operation extends to rear head gear that serves to hold the welding helmet on the head of the welder or to a location on the head of the welder between the head gear and the rear edge of the welding helmet.

15. The system of claim 14, wherein the curtain is made of a fire-resistant fabric.

16. The system of claim 14, wherein the curtain is made of a flexible molded material.

17. The system of claim 14, comprising an elastic front edge formed on or in the curtain and configured to urge the curtain towards the welding helmet.

18. The system of claim 17, comprising a pair of securement members extending from the front edge and configured to hook to a structure of the welding helmet to hold the front edge of the curtain adjacent to the rear edge of the welding helmet.

19. The system of claim 14, comprising a hook and loop fastener arrangement on a front edge of the curtain and the rear edge of the welding helmet configured to hold the front edge of the curtain adjacent to the rear edge of the welding helmet.

20. The system of claim 14, wherein the edge includes a hem formed in the curtain and an elastic band disposed in the hem.

* * * * *